(12) United States Patent
Kamata et al.

(10) Patent No.: US 10,151,734 B2
(45) Date of Patent: Dec. 11, 2018

(54) DATA PROCESSING SYSTEM AND METHOD FOR CHROMATOGRAPH

(71) Applicant: SHIMADZU CORPORATION, Kyoto-shi, Kyoto (JP)

(72) Inventors: Etsuho Kamata, Kameoka (JP); Toshinobu Yanagisawa, Kyoto (JP); Yasuhiro Mito, Kyotanabe (JP); Kenichi Mishima, Kameoka (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 273 days.

(21) Appl. No.: 14/915,794

(22) PCT Filed: Sep. 2, 2013

(86) PCT No.: PCT/JP2013/073555
§ 371 (c)(1),
(2) Date: Mar. 1, 2016

(87) PCT Pub. No.: WO2015/029254
PCT Pub. Date: Mar. 5, 2015

(65) Prior Publication Data
US 2016/0216240 A1    Jul. 28, 2016

(51) Int. Cl.
*G01N 30/74*    (2006.01)
*G01N 30/86*    (2006.01)

(52) U.S. Cl.
CPC ......... *G01N 30/8634* (2013.01); *G01N 30/74* (2013.01)

(58) Field of Classification Search
CPC . G01N 30/8634; G01N 30/74; G01N 30/8651
See application file for complete search history.

(56) References Cited

U.S. PATENT DOCUMENTS

| 4,674,323 A * | 6/1987 | Rulf ................. G01N 30/88 422/70 |
| 4,941,101 A * | 7/1990 | Crilly ............... G01N 30/8624 702/32 |
| 2002/0062683 A1* | 5/2002 | Ishii ................. G01N 30/8624 73/61.52 |
| 2015/0308992 A1* | 10/2015 | Yanagisawa ....... G01N 30/8675 702/25 |
| 2016/0146766 A1* | 5/2016 | Leszczyszyn ......... F16B 7/0406 204/452 |

(Continued)

OTHER PUBLICATIONS

Written Opinion for PCT/JP2013/073555 dated Dec. 10, 2013. [PCT/ISA/237].

(Continued)

*Primary Examiner* — Christine Enad
(74) *Attorney, Agent, or Firm* — Sughrue Mion, PLLC (57) ABSTRACT

A data processing system for a chromatograph including a standard sample data storage section; a standard sample sensitivity factor calculator; a post-correction standard sample chromatogram strength calculator; a specific designated retention time and specific designated wavelength setter; a measurement sample data storage section; a measurement sample sensitivity factor calculator; and a post-correction measurement sample chromatogram creator.

17 Claims, 8 Drawing Sheets

(56) References Cited

U.S. PATENT DOCUMENTS

2016/0169848 A1* 6/2016 Kamata .............. G01N 30/8634
                                                    702/32
2017/0160136 A1* 6/2017 Spartz ...................... G01J 3/42

OTHER PUBLICATIONS

"The Ministry of Health, Labour and Welfare Ministerial Notification No. 65", The Japanese Pharmacopoeia, Mar. 24, 2011, Sixteenth Edition.
International Search Report of PCT/JP2013/073555 dated Dec. 10, 2013.

* cited by examiner

| Dynamic Range Expansion Parameter Search | | | |
|---|---|---|---|
| Setting Parameter | Set Value | Search Range: Step | Found Value |
| Correction Wavelength Setting Method | ○Manual ●Auto | | |
| Correction Wavelength (Auto) | | | |
| Correction Wavelength (Auto) Strength | 200 | 100~700 : 1 | xxx |
| Correction Wavelength (Auto) Movement Direction | ●+ ○− | | |
| Strength for Extracting the Sensitivity Correction Spectrum | 500 | 200~900 : 1 | xxx |
| Background Correction | ●Yes ○No | | |

| Calculation Items | Use for Determination | Calculated Result |
|---|---|---|
| Correlation Coefficient of Calibration Curve | ☑ | x.xxxxxx |
| Deviation % Average | ☐ | |
| Deviation % Largest Value | ☐ | |

Begin Search

OK

Cancel

DATA PROCESSING SYSTEM AND METHOD FOR CHROMATOGRAPH

CROSS REFERENCE TO RELATED APPLICATIONS

This application is a National Stage of International Application No. PCT/JP2013/073555 filed Sep. 2, 2013, the contents of all of which are incorporated herein by reference in their entirety.

TECHNICAL FIELD

The present invention relates to a data processing system and data processing method for a chromatograph apparatus, such as a liquid chromatograph or gas chromatograph.

BACKGROUND ART

In a chromatograph apparatus, a set of data representing a chromatogram with the horizontal axis indicating time and the vertical axis indicating the signal strength (e.g. output voltage) are obtained by analyzing a sample (such data are hereinafter called the "chromatogram data"). A data processing system for a chromatograph detects a peak appearing on such a chromatogram, identifies a substance corresponding to that peak from the peak position (retention time) with reference to a previously set identification table, and calculates the concentration and/or quantity of the substance from the height and/or area of the peak.

Such a data processing system normally has limits on the magnitude of the signal that can be processed, due to hardware limitations of the signal-processing circuits including an A/D converter. The system cannot correctly perform calculations if the magnitude of the input signal is higher than the upper limit or lower than the lower limit.

Besides such a limitation related to signal processing, there is a problem that the reliability of the detection result obtained with a detector of a chromatograph apparatus varies with the signal level of the detector. For example, in a device used as a detector for a liquid chromatograph (such as an ultraviolet-visible spectrophotometer or photodiode array detector), if the concentration of the component in the sample is too low, the accuracy of the quantitative determination deteriorates due to the influence of noise in the detection signal. Conversely, if the component concentration is too high, the non-linearity of the detection signal becomes noticeable, so that the accuracy of the quantitative determination similarly deteriorates. Accordingly, when an analysis is performed with a conventional chromatograph apparatus, the sample needs to be appropriately diluted so that the component concentrations in the sample will be included in a predetermined range (dynamic range).

CITATION LIST

Non Patent Literature

Non Patent Literature 1: The Japanese Pharmacopoeia, Sixteenth Edition, [online], Mar. 24, 2011, The Ministry of Health, Labor and Welfare, [accessed on Jun. 21, 2013], the Internet

SUMMARY OF INVENTION

Technical Problem

In the case where the sample contains a plurality of components to be analyzed, if the concentrations of those components are not significantly varied, the analysis parameters (e.g. the concentration of the sample and the sensitivity of the detector) only need to be set so that all of the target components will be included in the dynamic range. By contrast, if there is a considerable difference in the concentration among the target components, it is impossible to correctly perform the analysis by any setting, since setting the parameters for correctly detecting the lowest-concentration component (impurity) causes deformation or saturation of the signal of the highest-concentration component (principal component), while setting the parameters for correctly detecting the highest-concentration component (principal component) causes the lowest-concentration component (impurity) to be obscured by noise.

For example, the Japanese Pharmacopeia, Sixteenth Edition (Non-Patent Literature 1) includes a section titled "Acetylcysteine: Purity Test (6) Related Substances" (pp. 311-312 in the Japanese version, or pp. 322-323 in the English version), which states that, as compared to the peak area of acetylcysteine, the area of each of the peaks other than acetylcysteine should not exceed 0.3% and the total area of the peaks should not exceed 0.6% in a test performed with a liquid chromatograph using an ultraviolet absorptiometer with the measurement wavelength set at 220 nm. In the case where there is such a large difference in concentration, if the sample is prepared with a high level of overall concentration (i.e. a low dilution ratio) in order to correctly determine the peak areas of the low-concentration components other than acetylcysteine, the signal of acetylcysteine will be deformed or saturated.

Such a situation has conventionally been addressed (i) by performing an analysis on each of a plurality of samples prepared with different concentrations, and correcting the obtained results according to their dilution ratios to determine the concentrations (or ratios of concentration) of the target components, or (ii) by setting two cells having different optical path lengths in two detectors, respectively, and performing an optical-path-length correction to determine the concentrations (or ratios of concentration) of the target components by a single analysis. However, method (i) is inefficient since it requires a considerable amount of time for the measurement, while method (ii) increases the cost of the device since it requires an additional detector.

The problem to be solved by the present invention is to provide a data processing system and data processing method for a chromatograph in which the data processing can be performed by a single analysis using a single detector, without being influenced by the noise in the detection signal or the non-linearity of the detection signal.

Solution to Problem

The data processing system for a chromatograph according to the present invention developed for solving the previously described problem is a data processing system for a chromatograph for creating a chromatogram based on a temporal change of a spectrum obtained within a wavelength range including a target wavelength corresponding to a target component, the system including:

a-1) a standard sample data storage section for storing a set of data of the spectrum for each of a plurality of standard samples having different concentrations of the target component;

a-2) a standard sample sensitivity factor calculator for calculating, for each of the standard samples, a standard sample sensitivity factor by dividing a first strength which is an strength at the target wavelength of the spectrum of the standard sample at a designated retention time common to all of the standard samples, by a second strength which is an strength at a designated wavelength which is within the aforementioned wavelength range and yet different from the target wavelength;

a-3) a post-correction standard sample chromatogram strength calculator for calculating, for each of the standard samples, a peak strength of a post-correction standard sample chromatogram obtained by multiplying a chromatogram at the designated wavelength by the standard sample sensitivity factor;

a-4) an index value calculator for calculating an index value showing the degree of correlation between the concentration of the standard sample and the peak strength of the post-correction standard sample chromatogram;

a-5) a specific designated retention time and specific designated wavelength setter for changing one or both of the designated retention time and the designated wavelength, for selecting a combination of the designated retention time and the designated wavelength at which the index value is within a predetermined range which indicates that the degree of correlation is high, as well as for setting the selected combination as a specific designated retention time and a specific designated wavelength;

b-1) a measurement sample data storage section for storing spectrum data of a measurement sample having an unknown concentration of the target component;

b-2) a measurement sample sensitivity factor calculator for calculating a measurement sample sensitivity factor by dividing a first strength which is an strength at the target wavelength of the spectrum of the measurement sample at the specific designated retention time by a second strength which is an strength of the same spectrum at the specific designated wavelength; and b-3) a post-correction measurement sample chromatogram creator for creating a post-correction measurement sample chromatogram by multiplying a chromatogram at the specific designated wavelength by the measurement sample sensitivity factor.

The data processing system for a chromatogram according to the present invention has the configuration described in a-1) through a-5) for specifying parameters used for creating a chromatogram using a plurality of standard samples having different (known) concentrations of the target component, and the configuration described in b-1) through b-3) for creating a chromatogram of a measurement sample having an unknown concentration of the target component using the aforementioned parameters. Hereinafter, the entire configuration of a-1) through a-5) is called the "parameter setter", while the entire configuration of b-1) through b-3) is called the "measurement sample chromatogram creator".

For the convenience of explanation, the measurement sample chromatogram creator is initially described.

Spectra of a component have a shape specific to that component. Therefore, if neither deformation nor saturation occurs, the spectra of the component obtained at any retention times within a chromatogram peak formed by that component are similar to each other in shape, and only their strengths differ from each other. Due to this similarity in the spectrum shape, it is possible to consider that, if chromatograms are created at a plurality of wavelengths belonging to one spectrum peak, the strength of each chromatogram is proportional to the strength of the spectrum at the wavelength corresponding to that chromatogram. Accordingly, for a spectrum of a measurement sample at a predetermined retention time (which is called the "designated retention time"), the measurement sample chromatogram creator performs the operation of multiplying the strength of the chromatogram at a wavelength which is different from the target wavelength and yet within the same spectrum peak (this wavelength is called the "designated wavelength") by the sensitivity factor which is the strength of the spectrum at the target wavelength divided by the strength of the same spectrum at the designated wavelength, i.e. the ratio of the strength of the spectrum at the target wavelength to the strength of the same spectrum at the designated wavelength. Due to the aforementioned similarity in shape, such an strength ratio of the spectrum is equal to the strength ratio between the chromatogram at the target wavelength and the chromatogram at the designated wavelength as long as the spectrum is neither deformed nor saturated. Therefore, even when the spectrum is deformed or saturated at retention times near the peak top of the chromatogram, a chromatogram in which the deformation or saturation is corrected (i.e. the post-correction measurement sample chromatogram) can be obtained with the same strength as the chromatogram at the target wavelength by specifying a designated wavelength and designated retention time at which such a saturation has not occurred.

Accordingly, in order to create a chromatogram which is neither deformed nor saturated, it is necessary to properly set the designated retention time and designated wavelength (which are called the "specific designated retention time" and "specific designated wavelength", respectively). This setting is performed by the parameter setter. Hereinafter, the parameter setter is described.

In the parameter setter, the designated retention time and designated wavelength are (provisionally) set for a plurality of standard samples having different concentrations of the target component. Subsequently, for each standard sample, the sensitivity factor ("standard sample sensitivity factor") is calculated, and the peak strength of a post-correction standard sample chromatogram obtained by multiplying the chromatogram at the (provisionally) designated wavelength by the standard sample sensitivity factor is calculated. After that, while one or both of the designated retention time and designated wavelength are changed, an index value (which will be described later) which shows the degree of correlation between the concentration of the standard sample and the peak strength of the post-correction standard sample chromatogram is calculated. Then, one combination of the designated retention time and designated wavelength at which the index value is within the predetermined range is selected and specified as the specific designated retention time and the specific designated wavelength. There can be a number of combinations of the designated retention time and designated wavelength at which the index value is within the predetermined range. In such a case, the combination which gives the best value of the index should preferably be selected from them, although it is also permissible to randomly select one of them and omit computations for making the best choice.

The previously described task of determining the relationship between the concentration of the standard sample and the peak strength of the chromatogram (the normal one and not the post-correction standard sample chromatogram) in the parameter setter corresponds to the task of creating a calibration curve. When creating a calibration curve, it is common to perform the measurement of the standard samples over a wider range of concentrations than is expected for the unknown sample so that the calibration curve can be used in the determination of the concentration of that unknown sample. This also applies in the present invention, and the specific designated retention time and specific designated wavelength are specified on the basis of data obtained by performing the measurement of the standard samples over such a wide range of concentrations.

Examples of the values available as the index value include (1) the absolute value of the correlation coefficient, (2) the average of the absolute value of the deviation at the peak strength of the post-correction standard sample chromatogram, and (3) the largest value of the absolute value of the aforementioned deviation. Two or more of these values may also be used in combination. These index values are hereinafter described.

(1) Correlation Coefficient

In the present invention, for a series of data $\{(d_i, I_i)\}$ (i=1, 2, ..., n) obtained for n kinds of standards samples having different concentrations of the target component (where n is a natural number equal to or greater than two) with $d_i$ denoting the concentration and $I_i$ denoting the peak strength of the post-correction standard sample chromatogram, the correlation coefficient C is given by:

$$C = \frac{\sum_{i=1}^{n}(d_i - d_{av})(I_i - I_{av})}{\sqrt{\sum_{i=1}^{n}(d_i - d_{av})^2}\sqrt{\sum_{i=1}^{n}(I_i - I_{av})^2}}$$

where $d_{av}$ and $I_{av}$ are the average values of the n pieces of data $\{d_i\}$ and $\{I_i\}$, respectively. The correlation coefficient C can take values ranging from −1 to +1. In general, a correlation coefficient C whose value is closer to +1 or −1 (i.e. whose absolute value is closer to 1) means that the two variables have a higher degree of correlation. However, the correlation coefficient of −1 means that an increase in one variable leads to a decrease in the other variable. As in the case of the present invention, when the concentration and peak strength are the two variables, the correlation coefficient must be closer to +1. Therefore, in the present invention, the designated retention time and designated wavelength at which the correlation coefficient C is closer to +1 than a predetermined value, i.e. greater than this predetermined value, are set as the specific designated retention time and specific designated wavelength.

(2) Average of Absolute Value of Deviation

For the previously mentioned series of data $\{(d_i, I_i)\}$ (i=1, 2, ..., n), a linear function I=kd (where k is a coefficient) showing the relationship between the concentration d and peak strength I is determined by an appropriate method (e.g. the least squares method). For each concentration $d_i$, the difference between the measured value $I_i$ of the peak strength I and the value $kd_i$ of the linear function, i.e. the deviation, is calculated. The designated retention time and designated wavelength at which the average of the absolute value of this deviation is equal to or smaller than the predetermined value are set as the specific designated retention time and specific designated wavelength.

(3) Largest Value of Absolute Value of Deviation

For the absolute values of the deviation calculated for each concentration $d_i$ in a similar manner to (2), the largest value among those values is used as the index value. The designated retention time and designated wavelength at which this largest value is equal to or smaller than a predetermined value are set as the specific designated retention time and specific designated wavelength.

The descriptions thus far have assumed that the data processing system for a chromatograph according to the present invention has both the parameter setter and the measurement sample chromatogram creator. It is possible to provide the data processing system for a chromatograph with only the parameter setter (i.e. the system performs only the creation of the calibration curve) and separately perform the creation of the chromatogram of the measurement sample based on the parameters set by the parameter setter.

The data processing method for a chromatograph according to the present invention is a data processing method for a chromatograph for creating a chromatogram based on a temporal change of a spectrum obtained within a wavelength range including a target wavelength corresponding to a target component, the method including the steps of:

calculating, for each of a plurality of standard samples having different concentrations of the target component, a standard sample sensitivity factor by dividing a first strength which is an strength at the target wavelength of the spectrum of the standard sample at a designated retention time common to all of the standard samples by a second strength which is an strength at a designated wavelength which is within the aforementioned wavelength range and yet different from the target wavelength;

calculating, for each of the standard samples, a peak strength of a post-correction standard sample chromatogram obtained by multiplying a chromatogram at the designated wavelength by the standard sample sensitivity factor;

calculating an index value showing the degree of correlation between the concentration of the standard sample and the peak strength of the post-correction standard sample chromatogram;

setting a specific designated retention time and a specific designated wavelength by changing one or both of the designated retention time and the designated wavelength, and by selecting a combination of the designated retention time and the designated wavelength at which the index value is within a predetermined range which indicates that the degree of correlation is high;

calculating, for a measurement sample having an unknown concentration of the target component, a measurement sample sensitivity factor by dividing a first strength which is an strength at the target wavelength of the spectrum of the measurement sample at the specific designated retention time by a second strength which is an strength of the same spectrum at the specific designated wavelength; and creating a post-correction measurement sample chromatogram by multiplying a chromatogram at the specific designated wavelength by the measurement sample sensitivity factor.

Advantageous Effects of the Invention

With the present invention, it is possible to process data obtained by an analysis using a chromatograph, by a single analysis using a single detector and without being influenced by the noise in the detection signal or the non-linearity of the detection signal. Since the designated retention time and designated wavelength which are necessary parameters for this data processing are automatically determined, even beginners can easily conduct the process.

DESCRIPTION OF EMBODIMENTS

One embodiment of the data processing system for a chromatograph according to the present invention is described using FIGS. 1-9. The following description deals with the case of a liquid chromatograph (LC). It should be noted that the description similarly applies in the case of a gas chromatograph.

Figure 1:
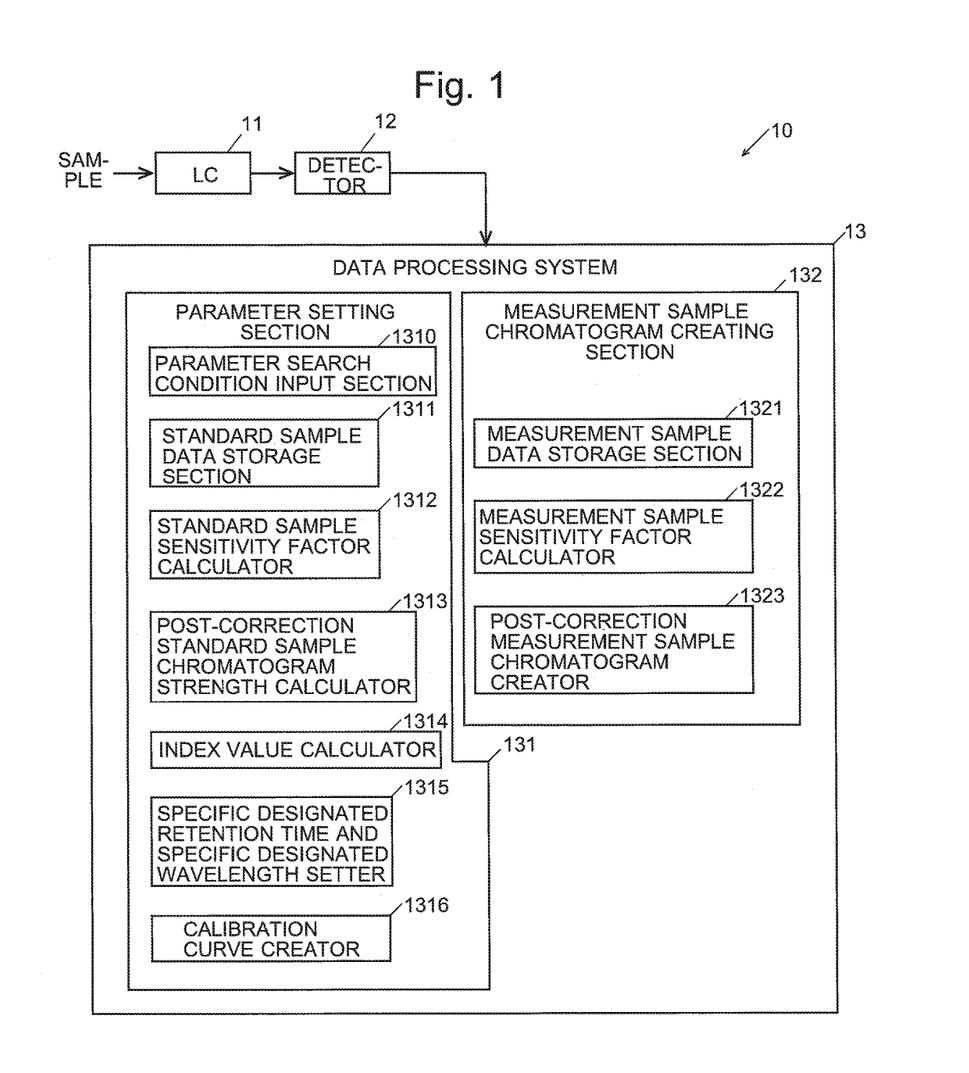
FIG. 1 is a schematic configuration diagram of an analyzing system including one embodiment of the data processing system for a chromatograph according to the present invention.

Embodiment (1) Configuration of Data Processing System for Chromatograph of Present Embodiment The data processing system for a chromatograph of the present embodiment constitutes a portion of the analyzing system shown in FIG. 1. The analyzing system 10 has an LC 11 for temporally separating the components contained in a liquid sample, a detector 12 for analyzing each of the separated components within a predetermined wavelength band, and a data processing system 13 for a chromatogram (the system of the present embodiment, which is hereinafter called the "data processing system") for processing data produced by the detector 12.

The data processing system 13 consists of a computer (hardware) and a dedicated data-processing software program installed on the same computer, where the computer is a commonly used computer having a CPU (central processing unit), storage device (a memory unit, hard disk, solid-state drive and/or other devices), display unit, input device (a keyboard, mouse and other devices) and other components. The data processing system 13 functions as a parameter setting section 131 and a measurement sample chromatogram creating section 132.

The parameter setting section 131 is provided for setting the aforementioned specific designated retention time and specific designated wavelength using the result of a measurement of a plurality of standard samples which respectively contain a target component at known and mutually different concentrations. This section has a parameter search condition input section 1310 for allowing users to input various conditions (which will be described later) for the setting, and a standard sample data storage section 1311 for storing measurement data of spectra at a large number of retention times for each of a plurality of different kinds of standard samples having different concentrations. The parameter setting section 131 also has a standard sample sensitivity factor calculator 1312, post-correction standard sample chromatogram strength calculator 1313, index value calculator 1314, specific designated retention time and specific designated wavelength setter 1315, and calibration curve creator 1316. These components will be explained when the operation of the data processing system 13 is described.

The measurement sample chromatogram creating section 132 has a measurement sample data storage section 1321, measurement sample sensitivity factor calculator 1322, and post-correction measurement sample chromatogram creator 1323, for performing a process using the result of a measurement performed on a measurement sample having an unknown concentration of the target component as well as the specific designated retention time and the specific designated wavelength, so as to eventually create a post-correction chromatogram of the measurement sample. The measurement sample data storage section 1321 is provided for storing measurement data of spectra at a large number of retention times for each measurement sample. The functions of the measurement sample sensitivity factor calculator 1322 and the post-correction measurement sample chromatogram creator 1323 will be described when the operation of the data processing system 13 is described.

Figure 2:
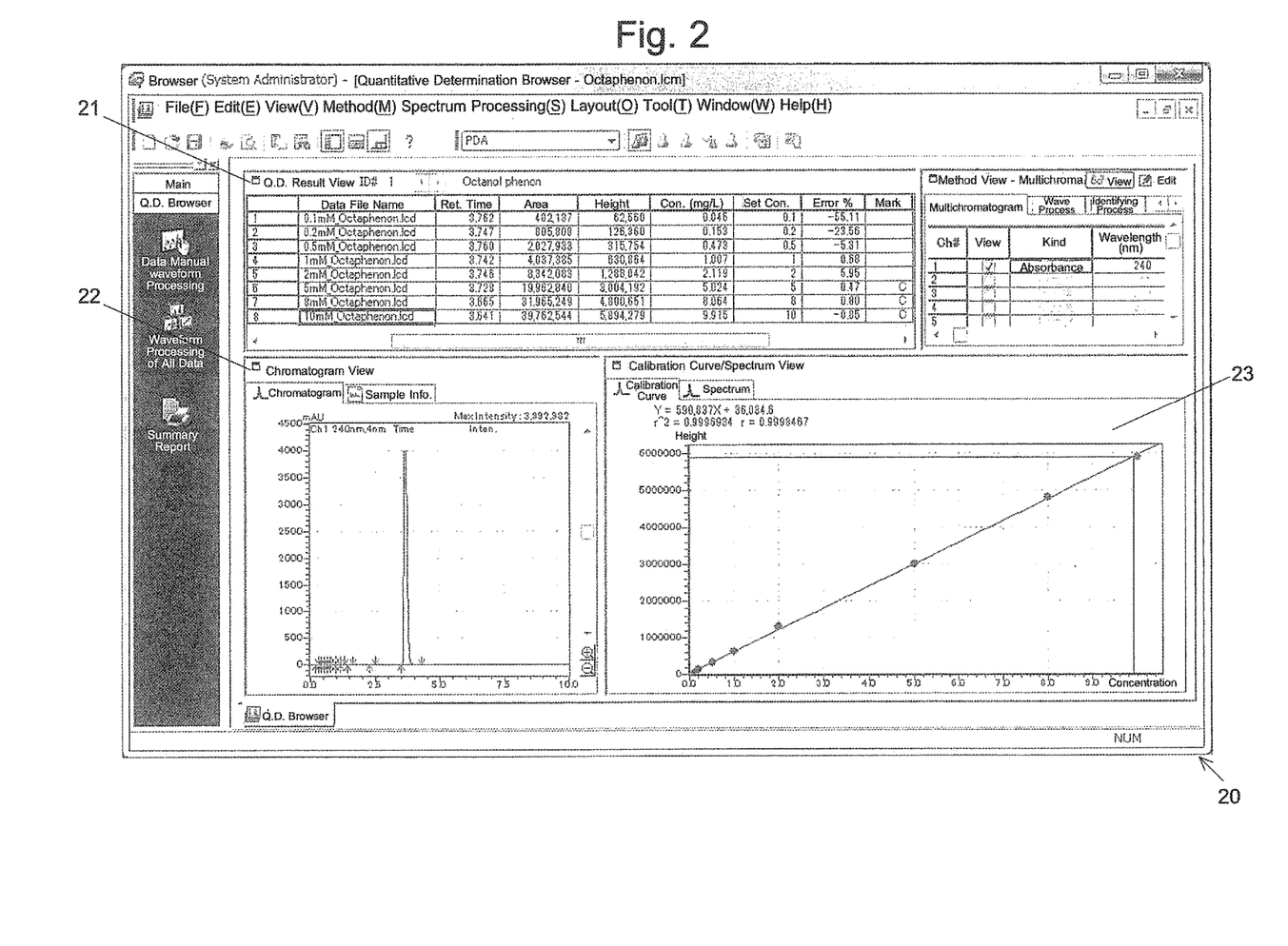
FIG. 2 shows one example of the quantitative determination browser window used for the parameter setting.
Figure 3:
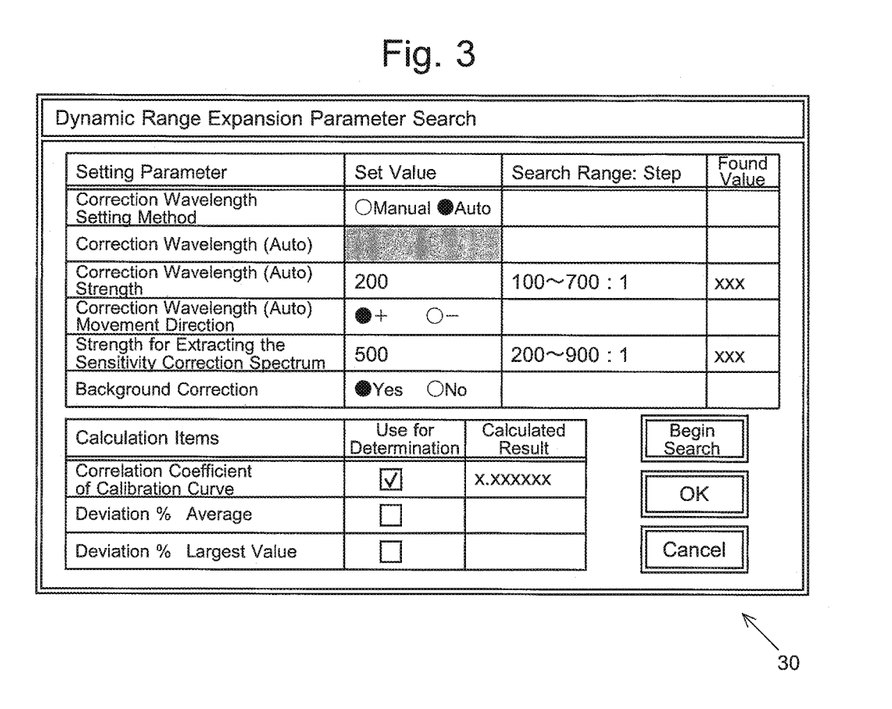
FIG. 3 shows one example of the parameter search condition input window used for the parameter setting.
Figure 4:
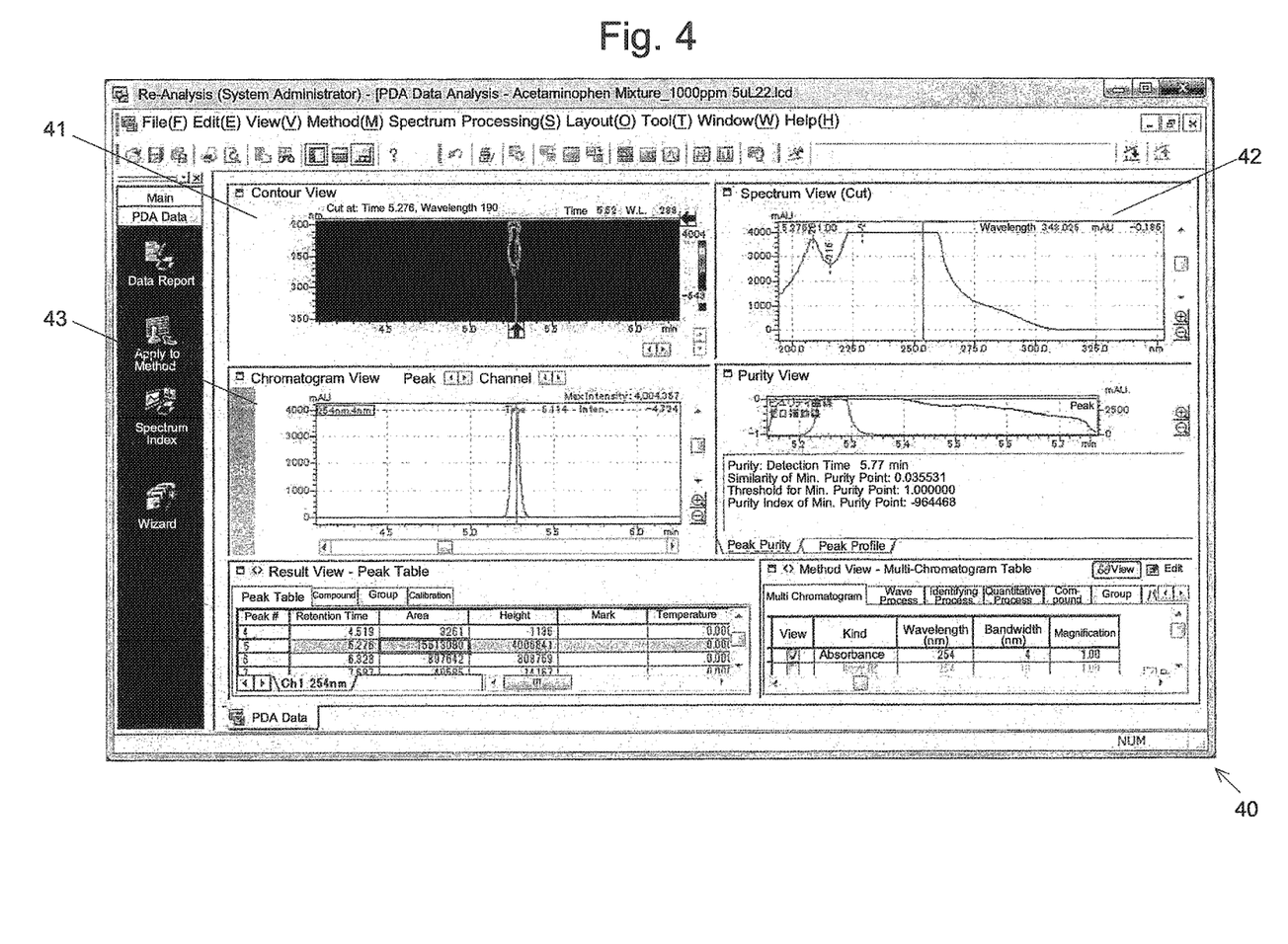
FIG. 4 shows one example of the data analyzing window used for creating a chromatogram of a measurement sample.

On the display unit of the data processing system 13, two windows are displayed: the quantitative determination browser window 20 as shown in FIG. 2 and the data analyzing window 40 as shown in FIG. 4. When a user performs a predetermined operation on the quantitative determination browser window 20, such as clicking a specific icon or selecting a specific item from the "Window (W)" pulldown menu, the parameter search condition input window 30 as shown in FIG. 3 is displayed. Hereinafter, the quantitative determination browser window 20, parameter search condition input window 30 and data analyzing window 40 are sequentially described.

The quantitative determination browser window 20 is a window to be used for the parameter setting using standard samples. It has a quantitative determination result view 21, chromatogram view 22, calibration curve/spectrum view 23, and other display areas. The quantitative result view 21 shows various items of information for each of a plurality of standard samples having known concentrations of the target component, such as the name of the data file, the area and height calculated from a chromatogram (the numerical values of the area and height can be changed by the data processing performed by the data processing system 13, which will be described later), as well as the concentration. The chromatogram view 22 shows a chromatogram of one kind of standard sample selected on the quantitative determination result view 21 by a user using a mouse or similar device. The tabs shown in the chromatogram view 22 allow the operation of switching the display to the detailed sample information stored in the data file related to the one kind of standard sample. The calibration curve/spectrum view 23 also has tabs for selectively displaying either a calibration curve or a spectrum of one standard sample at one retention time. The calibration curve is a graph showing the relationship between the concentration of the standard sample and the strength (area or height) of the chromatogram. This graph is used for determining the concentration of a measurement sample having an unknown concentration from the strength of a chromatogram of the measurement sample. The calibration curve can be changed by the data processing performed by the data processing system 13 (which will be described later).

The parameter search condition input window 30 is a window for allowing users to input the conditions for the parameter setting using the standard samples and execute an automatic search of the parameters.

Displayed in the upper portion of the parameter search condition input window 30 are the input fields of the "Correction Wavelength Setting Method", "Correction Wavelength (Manual)", "Correction Wavelength (Auto) Strength", "Correction Wavelength (Auto) Movement Direction", "Strength for Extracting the Sensitivity Correction Spectrum" and "Background Correction". In the "Correction Wavelength Setting Method" input field, the radio buttons for allowing users to select whether the aforementioned specific designated wavelength should be set automatically or manually are displayed. When "Auto" is selected, the data processing system 13 functions as one embodiment of the present invention. The "Correction Wavelength (Manual)" input field is a field which is enabled to allow users to input a numerical value of the specific designated wavelength when "Manual" is selected in the "Correction Wavelength Setting Method" input field. This case is unrelated to the embodiment of the present invention, and therefore, will not be described in detail. Detailed descriptions of the "Correction Wavelength (Auto) Strength" input field, "Correction Wavelength (Auto) Movement Direction" input field, "Strength for Extracting the Sensitivity Correction Spectrum" input field, and "Background Correction" input field will be made when the operation of the data processing system 13 is described.

In the lower portion of the parameter search condition input window 30, a field for selecting the calculation method for determining the index value showing the degree of correlation between the concentration of the standard sample and the aforementioned strength of the post-correction standard sample chromatogram is displayed. In the present embodiment, one or more indices can be selected from three kinds of indices: the correlation coefficient of the calibration curve, the average of the deviation, and the largest value of the deviation. Additionally, a set of buttons are displayed in the parameter search condition input window 30, including the "Begin Search" button for commanding the system to initiate the automatic parameter search after the input of the aforementioned conditions is completed.

The data analyzing window 40 is a window used for processing the data of the measurement sample. It has the contour view 41, spectrum view 42, chromatogram view 43, and other display areas. The contour view 41 shows the signal strength of the detector 12 by contour lines on a graph with the horizontal axis indicating the retention time and the vertical axis indicating the wavelength of the light detected with the detector 12. The spectrum view 42 shows the spectrum of the measurement sample at a specific retention time. The chromatogram view 43 shows a post-correction chromatogram of the measurement sample.

(2) Method for Correcting Saturation and Deformation of Chromatogram

Before the operation of the data processing system for a chromatograph according to the present embodiment is described, the method used in the system in order to correct saturation and deformation which can occur in a chromatogram is described using FIGS. 5A, 5B, 5C, 5D. This correction method is applied to both of the standard sample data and measurement sample data.

Figure 5A:
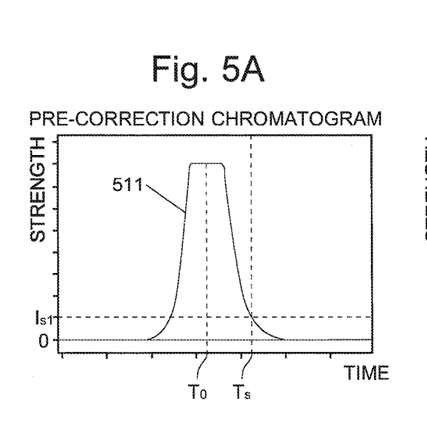
FIGS. 5A, 5B, 5C, and 5D illustrate a method used in the data processing system for a chromatograph of the present embodiment, for removing noise components of detection signals in the data for creating a chromatogram.
Figure 5B:
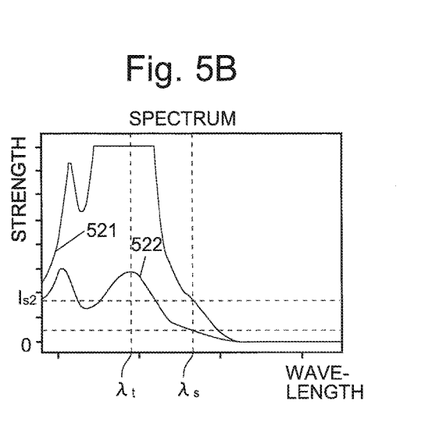

In general, if the concentration of the target component in the sample is too high, the pre-correction chromatogram 511 becomes saturated or deformed at a retention time $T_0$ included in a certain range, as shown in FIG. 5A. Such a saturation of the pre-correction chromatogram 511 occurs due to the saturation of the spectrum 521 at the retention time $T_0$ (which is hereinafter called the "first spectrum"), as shown in FIG. 5B. Since all spectra of one target component have a specific shape to that component, if neither the saturation nor deformation occurs, these spectra become similar to each other in shape and merely differ from each other in their strengths. By using this similarity, the saturation or deformation of the pre-correction chromatogram 511 is corrected as follows:

Initially, one retention time $T_s$ at which the pre-correction chromatogram 511 is not saturated is designated (FIG. 5A). This retention time $T_s$ is called the "designated retention time". The designated retention time $T_s$ may be directly designated. However, it is also possible to select an strength $I_{s1}$ on the pre-correction chromatogram 511 and thereby designate the point in time corresponding to that strength as the designated retention time, since it is when the strength is equal to or lower than a predetermined level that the pre-correction chromatogram 511 does not saturate. The value entered in the aforementioned "Strength for Extracting the Sensitivity Correction Spectrum" input field in the parameter search condition input window 30 corresponds to the strength $I_{s1}$ selected for this purpose. The spectrum 522 at this designated retention time $T_s$ (which is hereinafter called the "second spectrum") is neither saturated nor deformed (FIG. 5B).

Subsequently, a wavelength $\lambda_s$ at which the first spectrum 521 is neither saturated nor deformed is specified (FIG. 5B). This wavelength $\lambda_s$ is called the "designated wavelength". Once again, instead of directly specifying the designated wavelength $\lambda_s$, it is possible to select an strength $I_{s2}$ equal to or lower than a predetermined level at which no saturation of the spectrum occurs and thereby designate the wavelength corresponding to that strength as the designated wavelength $\lambda_s$. The value entered in the aforementioned "Correction Wavelength (Auto) Strength" input field in the parameter search condition input window 30 corresponds to the strength $\lambda_{s2}$ selected for this purpose.

Figure 5C:
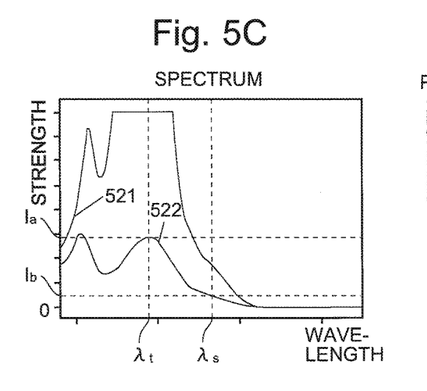

After that, the first strength $I_a$, which is the strength of the second spectrum 522 at the target wavelength $\lambda_t$ at which the spectrum of the target compound is maximized (normally, if the kind of target component is known, this wavelength is also known), and the second strength $I_b$, which is the strength of the second spectrum 522 at the designated wavelength $\lambda_s$, are determined (FIG. 5C). Then, the sensitivity factor, i.e. the ratio of the first strength $I_a$ to the second strength b, is calculated by $K=I_a/I_b$.

Figure 5D:
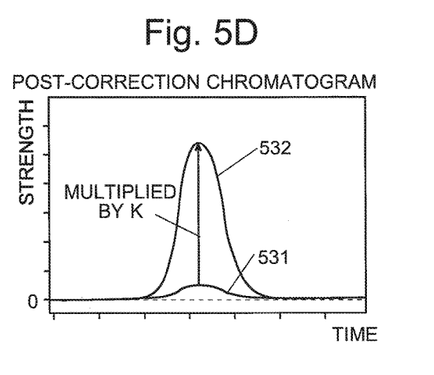

Due to the previously described similarity of the spectra, the ratio of the first strength $I_a$ to the second strength $I_b$ on the second spectrum 522 is equal to the ratio of the strength of the first spectrum 521 at the target wavelength $\lambda_t$ to the strength of the same spectrum at the designated wavelength $\lambda_s$. Accordingly, by creating a chromatogram 531 at the designated wavelength $\lambda_s$ at which the first spectrum 521 is neither saturated nor deformed, and then multiplying the chromatogram 531 by the sensitivity factor K, a post-correction chromatogram 532 which is neither saturated nor deformed at the target wavelength $\lambda_t$ can be obtained.

Figure 6:
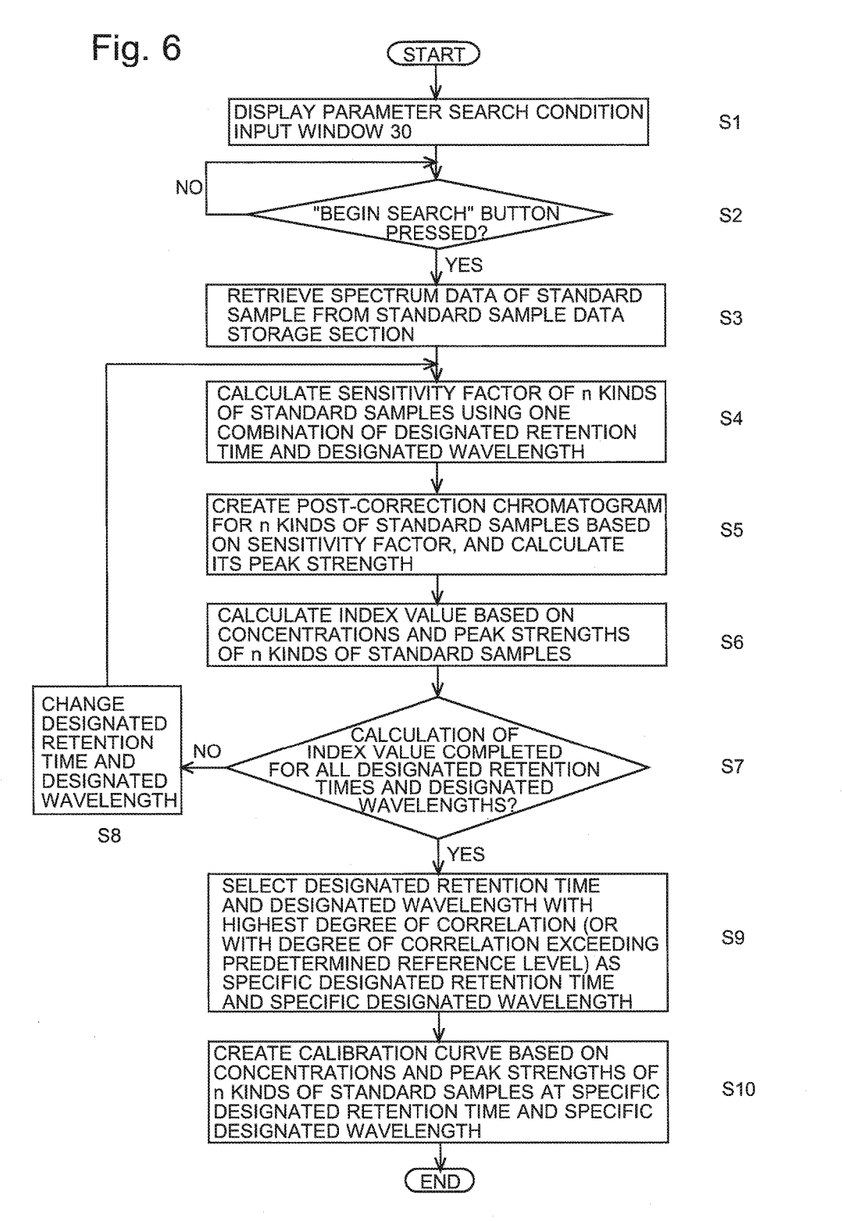
FIG. 6 is a flowchart for explaining an operation of the parameter setter in the data processing system for a chromatograph of the present embodiment.
Figure 7A:
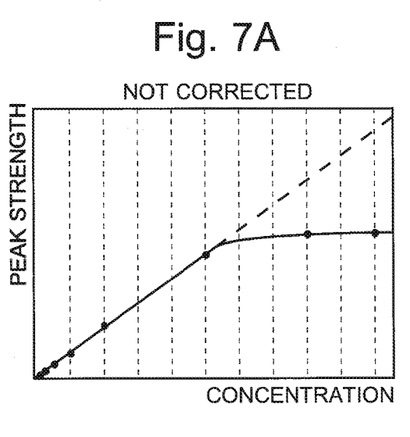
FIG. 7A is a calibration curve in the case where the chromatogram is not corrected.
Figure 7B:
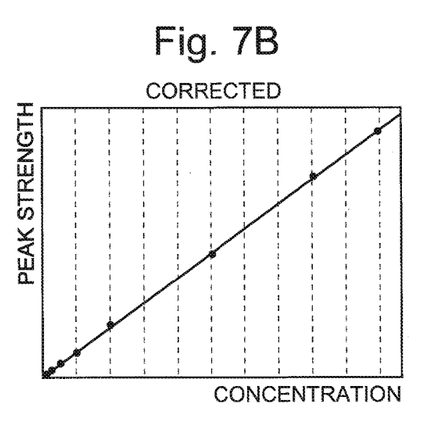
FIG. 7B is a calibration curve obtained after the chromatogram is corrected by the method of the present embodiment.
Figure 8:
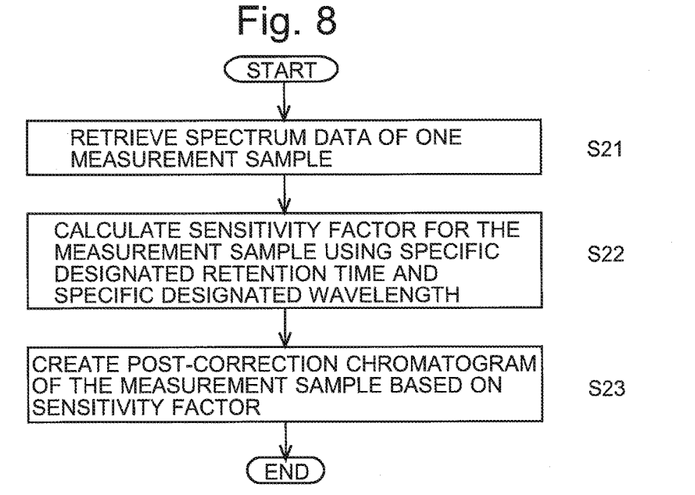
FIG. 8 is a flowchart for explaining an operation of the measurement sample chromatogram creator in the data processing system for a chromatograph of the present embodiment.
Figure 9:
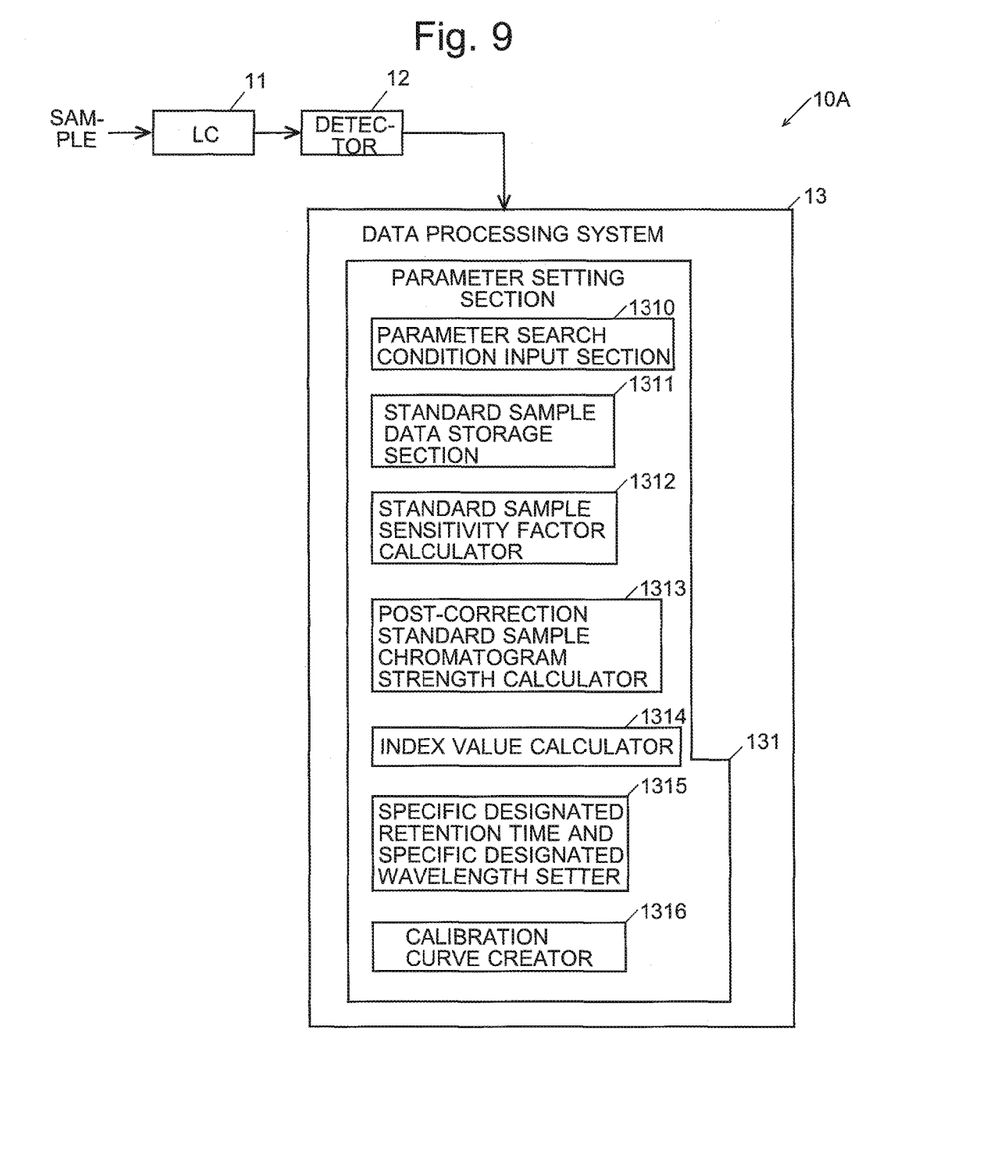
FIG. 9 a schematic configuration diagram showing another embodiment of the data processing system for a chromatograph according to the present invention.

(3) Operation of Data Processing System for Chromatograph of Present Embodiment An operation of the data processing system 13 is hereinafter described using the flowcharts of FIGS. 6 and 8 as well as the drawing of the calibration curve of FIG. 7.

(3-1) Operation of Parameter Setting Section 131

Initially, when the user performs the aforementioned predetermined operation on the quantitative determination browser window 20, the parameter search condition input section 1310 displays the parameter search condition input window 30 on the display unit (Step S1) and stands by until the user presses the "Begin Search" button after completing the input of the various conditions (Step S2).

On the parameter search condition input window 30, the user selects "Auto" in the "Correction Wavelength Setting Method" input field as well as inputs the setting values of the previously described strength $I_{s1}$ for extracting the sensitivity correction spectrum and the correction wavelength (auto) strength $I_{s2}$ into the "Strength for Extracting the Sensitivity Correction Spectrum" and "Correction Wavelength (Auto) Strength" input fields, respectively. It should be noted that these values are merely set as initial values; the optimum values are eventually determined by the data processing system 13 of the present embodiment. The user also inputs, into the "Strength for Extracting the Sensitivity Correction Spectrum" and "Correction Wavelength (Auto) Strength" input fields, numerical values which define the search range within which the strength $I_{s1}$ for extracting the sensitivity correction spectrum and the correction wavelength (auto) strength $I_{s2}$ are varied in the calculation of the optimum values by the data processing system 13, as well as a numerical value which defines the search step (interval) to vary those strength values. Additionally, the user inputs, into the "Background Correction" input field, whether or not the background correction is to be performed. The background correction is commonly performed in the data processing of chromatograms, and therefore, will not be described in the present embodiment. Furthermore, in the lower portion of the parameter search condition input window 30, the user selects the calculation method for determining the index value showing the degree of correlation between the concentration of the standard sample and the aforementioned strength of the post-correction standard sample chromatogram.

In some cases, the wavelength corresponding to the correction wavelength (auto) strength $I_{s2}$ is present on each of the longer and shorter wavelength sides of the target wavelength $\lambda_t$. To deal with such a case, the user specifies, in the "Correction Wavelength (Auto) Movement Direction" input field, which side of the wavelength should be selected. It is possible to input one designated retention time $T_s$ instead of the strength $I_{s1}$ for extracting the sensitivity correction spectrum. Similarly, it is possible to input one designated wavelength $\lambda_s$ instead of the correction wavelength (auto) strength $I_{s2}$.

After the input of these values has been completed, the user presses the "Begin Search" button, whereupon the process goes to Step S3. In Step S3, the standard sample sensitivity factor calculator 1312 retrieves spectrum data for each of a plurality of kinds of standard samples from the standard sample data storage section 1311. Next, for each standard sample, the standard sample sensitivity factor calculator 1312 calculates the sensitivity factor K described in (2), using one combination of the designated retention time $T_s$ and designated wavelength $\lambda_s$ (Step S4). Subsequently, for each standard sample, the post-correction standard sample chromatogram strength calculator 1313 creates the post-correction chromatogram 532 as described in (2) based on the sensitivity factor K obtained in Step S4, and calculates the peak strength (either the area strength of the peak or the peak-top strength) of the post-correction chromatogram 532 (Step S5).

By the operations described thus far, a series of data $\{(d_i, I_i)\}$ (i=1, 2, ..., n) with $d_i$ denoting the concentrations of n kinds of standard samples and $I_i$ denoting the peak strengths of the post-correction chromatograms 532 of those standard samples are obtained for one combination of the designated retention time $T_s$ and designated wavelength $\lambda_s$. Accordingly, the index value calculator 1314 calculates the index value at this combination of the designated retention time $T_s$ and designated wavelength $\lambda_s$ (Step S6). In the present embodiment, the index value selected by the user in the parameter search condition input window 30 is calculated, i.e. the correlation coefficient of the calibration curve, the average of the deviation, or the largest value of the deviation. Among these indices, the correlation coefficient of the calibration curve is calculated by the previously described calculation formula of the correlation coefficient C. The average or largest value of the deviation is calculated by determining the deviations by a commonly known method and taking an average or largest value of those deviations. In the case of the correlation coefficient C, a larger value means a higher degree of correlation. In the case of the average or largest value of the deviation, a smaller value means a higher degree of correlation.

After the index value for one combination of the designated retention time $T_s$ and designated wavelength $\lambda_s$ has been calculated, the index value calculator 1314 checks whether or not the calculation of the index value has been completed for all combinations of the designated retention time $T_s$ and designated wavelength $\lambda_s$ corresponding to the search range and search step entered by the user in the parameter search condition input window 30 (Step S7). If the calculation is completed, the process goes to Step S9. If the calculation is not completed, the designated retention time $T_s$ and designated wavelength Xs are changed to a new combination for which the calculation of the index value has not been completed (Step S8), and the operations of Steps S4 through S6 are repeated.

In Step S9, the specific designated retention time and specific designated wavelength setter 1315 selects, from among the plurality of combinations of the designated retention time $T_s$ and designated wavelength $\lambda_s$ obtained in the previously described process, the combination of the designated retention time $T_s$ and designated wavelength $\lambda_s$ at which the index value indicates the highest degree of correlation, as the specific designated retention time and specific designated wavelength. It is also possible to randomly select, from among the combinations of the designated retention time $T_s$ and designated wavelength $\lambda_s$ at which the index value has exceeded a predetermined reference level, one combination of the designated retention time $T_s$ and designated wavelength $\lambda_s$ as the specific designated retention time and specific designated wavelength. The strength values corresponding to the specific designated retention time and specific designated wavelength, as well as the calculated result of the correlation coefficient are displayed in the corresponding fields in the search condition input window 30.

Subsequently, the calibration curve creator 1316 creates the calibration curve based on the series of data $\{(d_i, I_i)\}$ obtained at the specific designated retention time and specific designated wavelength which have been determined. Before the correction of the chromatogram, the data points deviate from the straight line of the linear function due to the saturation of the chromatogram peak (FIG. 7A). By contrast, the calibration curve obtained in the present embodiment considerably agrees with the straight line of the linear function (FIG. 7B). The calibration curve creator 1316 displays the obtained post-correction calibration curve in the calibration curve/spectrum view 23 of the quantitative determination browser window 20.

With this, the operation of the parameter setting section 131 is discontinued.

(3-2) Operation of Measurement Sample Chromatogram Creating Section 132

When the user performs a predetermined operation for specifying one measurement sample having an unknown concentration of the target component on the data analyzing window 40, the measurement sample chromatogram creating section 132 begins its operation. Initially, the measurement sample sensitivity factor calculator 1322 retrieves the spectrum data of the measurement sample from the measurement sample data storage section 1321 (Step S21). Next, the measurement sample sensitivity factor calculator 1322 computes the sensitivity factor K described in (2), using the specific designated retention time and specific designated wavelength selected by the parameter setting section 131 as $T_s$ and $\lambda_s$, respectively (Step S22). Subsequently, the post-correction measurement sample chromatogram creator 1323 creates the post-correction chromatogram 532 of the measurement sample as described in (2) based on the sensitivity factor K obtained in Step S22 (Step S23). With this, the operation of the measurement chromatogram creating section 132 is discontinued.

The present invention is not limited to the previous embodiment.

For example, in the previous embodiment, the calibration curve creator 1316 in the parameter setting section 131 creates a calibration curve based on the data obtained at the specific designated retention time and specific designated wavelength. However, the calibration curve creator 1316 is dispensable if the purpose of the system is to merely select the specific designated retention time and specific designated wavelength. Conversely, if the purpose is to create the calibration curve without being affected by the saturation or deformation of the chromatogram, a configuration having the parameter setting section 131 without including the measurement sample chromatogram creating section 132 may be adopted, as in the case of the analyzing system 10A shown in FIG. 9.

REFERENCE SIGNS LIST

10, 10A . . . Analyzing System
11 . . . LC
12 . . . Detector
13 . . . Data Processing System
131 . . . Parameter Setting Section
1310 . . . Parameter Search Condition Input Section
1311 . . . Standard Sample Data Storage Section
1312 . . . Standard Sample Sensitivity Factor Calculator
1313 . . . Post-Correction Standard Sample Chromatogram Strength Calculator
1314 . . . Index Value Calculator
1315 . . . Specific Designated Retention Time and Specific Designated Wavelength Setter
1316 . . . Calibration Curve Creator
132 . . . Measurement Sample Chromatogram Creating Section
1321 . . . Measurement Sample Data Storage Section
1322 . . . Measurement Sample Sensitivity Factor Calculator
1323 . . . Post-Correction Measurement Sample Chromatogram Creator
20 . . . Quantitative Determination Browser Window
21 . . . Quantitative Determination Result View
22 . . . Chromatogram View
23 . . . Calibration Curve/Spectrum View
30 . . . Parameter Search Condition Input Window
40 . . . Data Analyzing Window
41 . . . Contour View
42 . . . Spectrum View
43 . . . Chromatogram View
511 . . . Pre-Correction Chromatogram
521 . . . First Spectrum
522 . . . Second Spectrum
531 . . . Chromatogram at Designated Wavelength k
532 . . . Post-Correction Chromatogram

The invention claimed is:

1. A data processing system for a chromatograph for creating a chromatogram based on a temporal change of a spectrum obtained within a wavelength range including a target wavelength corresponding to a target component, the system comprising:

a-1) a standard sample data storage section that is implemented by a memory and configured for storing a set of data of the spectrum for each of a plurality of standard samples having different concentrations of the target component;

a-2) a standard sample sensitivity factor calculator that is implemented by a processor and configured for calculating, for each of the standard samples, a standard sample sensitivity factor by dividing a first strength which is an strength at the target wavelength of the spectrum of the standard sample at a designated retention time common to all of the standard samples, by a second strength which is an strength at a designated wavelength which is within the aforementioned wavelength range and yet different from the target wavelength;

a-3) a post-correction standard sample chromatogram strength calculator that is implemented by the processor and configured for calculating, for each of the standard samples, a peak strength of a post-correction standard sample chromatogram obtained by multiplying a chromatogram at the designated wavelength by the standard sample sensitivity factor;

a-4) an index value calculator that is implemented by the processor and configured for calculating an index value showing a degree of correlation between the concentration of the standard sample and the peak strength of the post-correction standard sample chromatogram;

a-5) a specific designated retention time and specific designated wavelength setter that is implemented by the processor and configured for changing one or both of the designated retention time and the designated wavelength, for selecting a combination of the designated retention time and the designated wavelength at which the index value is within a predetermined range which indicates that the degree of correlation is high, as well as for setting the selected combination as a specific designated retention time and a specific designated wavelength;

b-1) a measurement sample data storage section that is implemented by the memory and configured for storing spectrum data of a measurement sample having an unknown concentration of the target component;

b-2) a measurement sample sensitivity factor calculator that is implemented by the processor and configured for calculating a measurement sample sensitivity factor by dividing a first strength which is an strength at the target wavelength of the spectrum of the measurement sample at the specific designated retention time by a second strength which is an strength of the same spectrum at the specific designated wavelength;

b-3) a post-correction measurement sample chromatogram creator that is implemented by the processor and configured for creating a post-correction measurement sample chromatogram by multiplying a chromatogram at the specific designated wavelength by the measurement sample sensitivity factor; and a user interface configured for receiving user input to be used in the creating the post-correction measurement sample chromatogram and for displaying the created post-correction measurement sample chromatogram.

2. The data processing system for a chromatograph according to claim 1, comprising a calibration curve creator for creating a calibration curve based on the concentration of the standard sample at the specified designated retention time and the specific designated wavelength as well as on the peak strength of the post-correction standard sample chromatogram.

3. The data processing system for a chromatograph according to claim 2, wherein the index value is a correlation coefficient C given by:

$$C = \frac{\sum_{i=1}^{n}(d_i - d_{av})(I_i - I_{av})}{\sqrt{\sum_{i=1}^{n}(d_i - d_{av})^2} \sqrt{\sum_{i=1}^{n}(I_i - I_{av})^2}}$$

where data $\{(d_i, I_i)\}$ (i=1, 2, . . . , n) are a series of data obtained for n kinds of standards samples having different concentrations of the target component (where n is a natural number equal to or greater than two) with $d_i$ denoting the concentration and $I_i$ denoting the peak strength of the post-correction standard sample chromatogram, $d_{av}$ is an average value of the concentration $d_i$, and $I_{av}$ is an average value of the peak strength $I_i$.

4. The data processing system for a chromatograph according to claim 3, wherein, for a linear function I=kd of concentration d and peak strength I (where k is a coefficient) determined based on a series of data $\{(d_i, I_i)\}$ (i=1, 2, . . . , n) obtained for n kinds of standards samples having different concentrations of the target component (where n is a natural number equal to or greater than two) with $d_i$ denoting the concentration and $I_i$ denoting the peak strength of the post-correction standard sample chromatogram, the index value is an average value or largest value of an absolute value of a deviation which is a difference between a value $kd_i$ of the linear function and the measured value $I_i$ of each standard sample.

5. The data processing system for a chromatograph according to claim 2, wherein, for a linear function I=kd of concentration d and peak strength I (where k is a coefficient) determined based on a series of data $\{(d_i, I_i)\}$ (i=1, 2, . . . , n) obtained for n kinds of standards samples having different concentrations of the target component (where n is a natural number equal to or greater than two) with $d_i$ denoting the concentration and $I_i$ denoting the peak strength of the post-correction standard sample chromatogram, the index value is an average value or largest value of an absolute value of a deviation which is a difference between a value $kd_i$ of the linear function and the measured value $I_i$ of each standard sample.

6. The data processing system for a chromatograph according to claim 1, wherein the index value is a correlation coefficient C given by:

$$C = \frac{\sum_{i=1}^{n}(d_i - d_{av})(I_i - I_{av})}{\sqrt{\sum_{i=1}^{n}(d_i - d_{av})^2} \sqrt{\sum_{i=1}^{n}(I_i - I_{av})^2}}$$

where data $\{(d_i, I_i)\}$ (i=1, 2, . . . , n) are a series of data obtained for n kinds of standards samples having different concentrations of the target component (where n is a natural number equal to or greater than two) with $d_i$ denoting the concentration and $I_i$ denoting the peak strength of the post-correction standard sample chromatogram, $d_{av}$ is an average value of the concentration $d_i$, and $I_{av}$ is an average value of the peak strength $I_i$.

7. The data processing system for a chromatograph according to claim 6, wherein, for a linear function I=kd of concentration d and peak strength I (where k is a coefficient) determined based on a series of data $\{(d_i, I_i)\}$ (i=1, 2, . . . , n) obtained for n kinds of standards samples having different concentrations of the target component (where n is a natural number equal to or greater than two) with $d_i$ denoting the concentration and $I_i$ denoting the peak strength of the post-correction standard sample chromatogram, the index value is an average value or largest value of an absolute value of a deviation which is a difference between a value $kd_i$ of the linear function and the measured value $I_i$ of each standard sample.

8. The data processing system for a chromatograph according to claim 1, wherein, for a linear function I=kd of concentration d and peak strength I (where k is a coefficient) determined based on a series of data $\{(d_i, I_i)\}$ (i=1, 2, . . . , n) obtained for n kinds of standards samples having different concentrations of the target component (where n is a natural number equal to or greater than two) with $d_i$ denoting the concentration and $I_i$ denoting the peak strength of the post-correction standard sample chromatogram, the index value is an average value or largest value of an absolute value of a deviation which is a difference between a value $kd_i$ of the linear function and the measured value $I_i$ of each standard sample.

9. A data processing system for a chromatograph for specifying a parameter used in a process of creating a chromatogram based on a temporal change of a spectrum obtained within a wavelength range including a target wavelength corresponding to a target component, the system comprising:

1) a standard sample data storage section that is implemented by a memory and configured for storing a set of data of the spectrum for each of a plurality of standard samples having different concentrations of the target component;

2) a standard sample sensitivity factor calculator that is implemented by a processor and configured for calculating, for each of the standard samples, a standard sample sensitivity factor by dividing a first strength which is an strength at the target wavelength of the spectrum of the standard sample at a designated retention time common to all of the standard samples, by a second strength which is an strength at a designated wavelength which is within the aforementioned wavelength range and yet different from the target wavelength;

3) a post-correction standard sample chromatogram strength calculator that is implemented by the processor and configured for calculating, for each of the standard samples, a peak strength of a post-correction standard sample chromatogram obtained by multiplying a chromatogram at the designated wavelength by the standard sample sensitivity factor;

4) an index value calculator that is implemented by the processor and configured for calculating an index value showing a degree of correlation between the concentration of the standard sample and the peak strength of the post-correction standard sample chromatogram;

5) a specific designated retention time and specific designated wavelength setter that is implemented by the processor and configured for changing one or both of the designated retention time and the designated wavelength, for selecting a combination of the designated retention time and the designated wavelength at which the index value is within a predetermined range which indicates that the degree of correlation is high, as well as for setting the selected combination as a specific designated retention time and a specific designated wavelength; and a user interface configured for receiving user input to be used in creating a post-correction measurement sample chromatogram based on the specific designated retention time and the specific designated wavelength, and for displaying the created post-correction measurement sample chromatogram.

10. The data processing system for a chromatograph according to claim 9, comprising a calibration curve creator for creating a calibration curve based on the concentration of the standard sample at the specified designated retention time and the specific designated wavelength as well as on the peak strength of the post-correction standard sample chromatogram.

11. The data processing system for a chromatograph according to claim 10, wherein the index value is a correlation coefficient C given by:

$$C = \frac{\sum_{i=1}^{n}(d_i - d_{av})(I_i - I_{av})}{\sqrt{\sum_{i=1}^{n}(d_i - d_{av})^2} \sqrt{\sum_{i=1}^{n}(I_i - I_{av})^2}}$$

where data $\{(d_i, I_i)\}$ (i=1, 2, ..., n) are a series of data obtained for n kinds of standards samples having different concentrations of the target component (where n is a natural number equal to or greater than two) with $d_i$ denoting the concentration and $I_i$ denoting the peak strength of the post-correction standard sample chromatogram, $d_{av}$ is an average value of the concentration $d_i$, and $I_{av}$ is an average value of the peak strength $I_i$.

12. The data processing system for a chromatograph according to claim 11, wherein, for a linear function I=kd of concentration d and peak strength I (where k is a coefficient) determined based on a series of data $\{(d_i, I_i)\}$ (i=1, 2, ..., n) obtained for n kinds of standards samples having different concentrations of the target component (where n is a natural number equal to or greater than two) with $d_i$ denoting the concentration and $I_i$ denoting the peak strength of the post-correction standard sample chromatogram, the index value is an average value or largest value of an absolute value of a deviation which is a difference between a value $kd_i$ of the linear function and the measured value $I_i$ of each standard sample.

13. The data processing system for a chromatograph according to claim 10, wherein, for a linear function I=kd of concentration d and peak strength I (where k is a coefficient) determined based on a series of data $\{(d_i, I_i)\}$ (i=1, 2, ..., n) obtained for n kinds of standards samples having different concentrations of the target component (where n is a natural number equal to or greater than two) with $d_i$ denoting the concentration and $I_i$ denoting the peak strength of the post-correction standard sample chromatogram, the index value is an average value or largest value of an absolute value of a deviation which is a difference between a value $kd_i$ of the linear function and the measured value $I_i$ of each standard sample.

14. The data processing system for a chromatograph according to claim 9, wherein the index value is a correlation coefficient C given by:

$$C = \frac{\sum_{i=1}^{n}(d_i - d_{av})(I_i - I_{av})}{\sqrt{\sum_{i=1}^{n}(d_i - d_{av})^2} \sqrt{\sum_{i=1}^{n}(I_i - I_{av})^2}}$$

where data $\{(d_i, I_i)\}$ (i=1, 2, ..., n) are a series of data obtained for n kinds of standards samples having different concentrations of the target component (where n is a natural number equal to or greater than two) with $d_i$ denoting the concentration and $I_i$ denoting the peak strength of the post-correction standard sample chromatogram, $d_{av}$ is an average value of the concentration $d_i$, and $I_{av}$ is an average value of the peak strength $I_i$.

15. The data processing system for a chromatograph according to claim 14, wherein, for a linear function I=kd of concentration d and peak strength I (where k is a coefficient) determined based on a series of data $\{(d_i, I_i)\}$ (i=1, 2, ..., n) obtained for n kinds of standards samples having different concentrations of the target component (where n is a natural number equal to or greater than two) with $d_i$ denoting the concentration and $I_i$ denoting the peak strength of the post-correction standard sample chromatogram, the index value is an average value or largest value of an absolute value of a deviation which is a difference between a value $kd_i$ of the linear function and the measured value $I_i$ of each standard sample.

16. The data processing system for a chromatograph according to claim 9, wherein, for a linear function I=kd of concentration d and peak strength I (where k is a coefficient) determined based on a series of data $\{(d_i, I_i)\}$ (i=1, 2, ..., n) obtained for n kinds of standards samples having different concentrations of the target component (where n is a natural number equal to or greater than two) with $d_i$ denoting the concentration and $I_i$ denoting the peak strength of the post-correction standard sample chromatogram, the index value is an average value or largest value of an absolute value of a deviation which is a difference between a value $kd_i$ of the linear function and the measured value $I_i$ of each standard sample.

17. A data processing method for a chromatograph for creating a chromatogram based on a temporal change of a spectrum obtained within a wavelength range including a target wavelength corresponding to a target component, the method comprising the steps of:
- calculating, for each of a plurality of standard samples having different concentrations of the target component, a standard sample sensitivity factor by dividing a first strength which is an strength at the target wavelength of the spectrum of the standard sample at a designated retention time common to all of the standard samples by a second strength which is an strength at a designated wavelength which is within the aforementioned wavelength range and yet different from the target wavelength;
- calculating, for each of the standard samples, a peak strength of a post-correction standard sample chromatogram obtained by multiplying a chromatogram at the designated wavelength by the standard sample sensitivity factor;
- calculating an index value showing a degree of correlation between the concentration of the standard sample and the peak strength of the post-correction standard sample chromatogram;
- setting a specific designated retention time and a specific designated wavelength by changing one or both of the designated retention time and the designated wavelength, and by selecting a combination of the designated retention time and the designated wavelength at which the index value is within a predetermined range which indicates that the degree of correlation is high;
- calculating, for a measurement sample having an unknown concentration of the target component, a measurement sample sensitivity factor by dividing a first strength which is an strength at the target wavelength of the spectrum of the measurement sample at the specific designated retention time by a second strength which is an strength of the same spectrum at the specific designated wavelength;
- creating a post-correction measurement sample chromatogram by multiplying a chromatogram at the specific designated wavelength by the measurement sample sensitivity factor; and
- displaying, on a user interface, the created post-correction measurement sample chromatogram,
- wherein the user interface is configured to receive user input to be used in the creating the post-correction measurement sample chromatogram.

* * * * *